United States Patent
Minyard et al.

(10) Patent No.: US 6,891,920 B1
(45) Date of Patent: May 10, 2005

(54) AUTOMATED BACKGROUND PROCESSING MAMMOGRAPHIC IMAGE DATA

(75) Inventors: Thomas J. Minyard, Golden, CO (US); Morgan W. Nields, Englewood, CO (US); Guy M. Besson, Broomfield, CO (US)

(73) Assignee: Fischer Imaging Corporation, Denver, CO (US)

( * ) Notice: Subject to any disclaimer, the term of this patent is extended or adjusted under 35 U.S.C. 154(b) by 0 days.

(21) Appl. No.: 10/307,215

(22) Filed: Nov. 29, 2002

(51) Int. Cl.[7] ............................................... A61B 6/04
(52) U.S. Cl. ........................... 378/37; 378/901; 382/128
(58) Field of Search ................... 378/37, 901; 382/128, 382/132; 345/807

(56) References Cited

U.S. PATENT DOCUMENTS

| | | | | |
|---|---|---|---|---|
| 5,970,164 A | * | 10/1999 | Bamberger et al. | 382/128 |
| 6,553,356 B1 | * | 4/2003 | Good et al. | 706/15 |
| 6,611,575 B1 | * | 8/2003 | Alyassin et al. | 378/37 |

2001/0038681 A1 * 11/2001 Stanton et al. ................ 378/55

* cited by examiner

Primary Examiner—Craig E. Church
Assistant Examiner—Irakli Kiknadze
(74) Attorney, Agent, or Firm—Marsh Fischmann & Breyfogle LLP

(57) ABSTRACT

Disclosed is a mammographic imaging system and tools for processing mammographic images to enhance image acquisition and review workflow. The systems and tools enable rapid access to digital image information providing for improved workflow management and identification of images, upon initial review. The system and tools also allow for background processing of image information to reduce workflow delay. Specifically, digital images are processed in the background, i.e., they are automatically processed, free from specific task-orientated direction by a user, using resources that are not otherwise occupied addressing user-directed tasks. Background processing that may be supported includes preprocessing and interim processing. Preprocessing refers to processing of an image that occurs prior to initial review of that image by a physician. Interim processing refers to background processing that occurs during a review session, e.g., in a time period between initial review and a subsequent review of an image.

30 Claims, 7 Drawing Sheets

US 6,891,920 B1

AUTOMATED BACKGROUND PROCESSING MAMMOGRAPHIC IMAGE DATA

FIELD OF THE INVENTION

The present invention relates generally to mammography and, in particular, to tools and associated processing of mammographic images for enhanced image acquisition and review workflow.

BACKGROUND OF THE INVENTION

Mammography, including x-ray imaging and other imaging modalities, is widely used in detection and analysis of cysts, lesions, microcalcifications and other areas of interest within a patient's breast. Because of its proved effectiveness in early detection and diagnosis, including detection and diagnosis of non-palpable lesions, mammography continues to be recommended for many women. As a result, mammography equipment is available in many locations and such equipment, as well as clinicians and physicians experienced in using such equipment and analyzing the mammographic images, are typically kept busy meeting the demand for mammographic services.

Currently, most x-ray mammography systems are been film-based, although digital systems are gradually becoming more common. Physicians' preferences for film-based or digital systems depend on associated workflow processing as well as screening and diagnostic efficacy. During screening, common image projection views, such as the cranial caudal (CC) and medial lateral oblique (MLO) views are typically obtained for each patient. For example, such images may be obtained in connection with an annual screening process. Images for many patients may be acquired, for example, over the course of day. In the case of film-based mammography, the associated films may then be organized for review by a physician. In some cases, such review may involve comparing current films for a patient to films acquired on prior visits. If something suspicious is identified as a result of the screening process, a physician may acquire additional images from that patient, resulting in a further office visit by the patient.

Film-based mammography has certain perceived advantages. First, film-based mammography equipment is readily available. In addition, many physicians and clinicians are familiar with the equipment and the resulting images such that retraining is minimized. Moreover, physicians have significant flexibility in organizing films for display on a lightbox and such reviews can be accomplished efficiently.

More recently, digital mammography has been gaining acceptance. In digital mammography, images are acquired digitally and can be displayed on electronic monitors.

A number of advantages associated with digital imaging have been recognized. First, digital imaging provides near real-time images. In some cases, additional views may be acquired based on near real-time review of the digital images such that a return visit by the patient can be avoided. In addition, digital processing allows for image enhancement. In this regard, a physician may zoom in on an area of interest, adjust the image contrast or brightness or otherwise manipulate the image after acquisition. Moreover, it is sometimes possible to obtain improved diagnostic information by digital processing. For example, a digital image that is identified as being suspicious or is otherwise of interest can be exported to certain CAD systems that perform digital analyses. For example, such CAD systems may perform a pixel-by-pixel analysis of the digital image to identify areas of reduced intensity that may be missed upon review of the images using the naked eye. Such areas may indicate microcalcifications or other conditions of interest that the physician may desire to review more closely, such as by zooming in on that region of the image or otherwise enhancing the image.

Despite these advantages, certain perceived disadvantages have slowed the process of full digital acceptance. Some of the perceived disadvantages are specific to particular digital imaging equipment. In this regard, some current digital imaging systems do not provide a full field of view for a patient's breast. As a result, multiple images may be required for a screening analysis or the digital imaging system may be relegated to follow-up imaging of an area identified by film or other applications such as stereotactic localization. In addition, some current digital imaging systems provide a limited resolution that may be deemed insufficient for certain applications. However, full field, high-resolution digital imaging systems are now being marketed, including the SenoScan™ system of Fischer Imaging Corp. of Thornton, Colo.

Other perceived disadvantages relate to inefficiencies in the manner that digital imaging equipment is used. Many conventional digital mammography systems are stand alone units that include the patient imaging station or gantry (e.g., the x-ray tube, compression paddle, detector and the like), a processor executing image processing logic and a display terminal that may include oversized high resolution monitors. In these cases, a physician may review images at the image acquisition site. This may tie up the equipment when needed or require that the physician plan around a schedule for accessing the equipment.

Moreover, many physicians feel that using an electronic monitor to review images is slower than reviewing films. In the case of films, a physician may review a large quantity of films in one session. The films may be arranged in an order designated by the physician. When the films are thus properly prepared, an experienced physician may be able to adequately analyze certain images or sets of images in a matter of seconds, while devoting a larger time period to a subset of images requiring further analysis. In the digital context, significant time may be spent retrieving and arranging images. Even after an image is identified for review, significant time may be required to load and display the image due to the large amount of information contained in a high quality image. These operational difficulties have resulted in some degree of resistance to digital mammography in spite of the potential advantages as noted above.

SUMMARY

The present invention is directed to tools and associated processing of mammographic images to enhance image acquisition and review workflow. In particular, the present invention enables rapid access to digital image information for improved workflow management and identification of images, upon initial review, for substantially instant recall at a later time. The invention also allows for background processing of image information for enhanced functionality substantially without workflow delay. The invention thus addresses certain perceived disadvantages of digital mammography while providing improved digital processing functionality, thereby providing additional digital advantages.

According to one aspect of the present invention, digital images are processed in the background, i.e., they are automatically processed, free from specific task-orientated direction by a user, using resources that are not otherwise occupied addressing user-directed tasks. The associated system includes image acquisition equipment for acquiring mammographic images from a patient, image review equipment for displaying images of the patient, and a processor for receiving imaging information from the acquisition equipment, processing the image information and making processed image information available to the image review equipment. The processor runs logic for identifying background tasks for particular images and executing the tasks in the background. The logic identifies at least one task and executes the task free from concurrent user prompts. In this manner, certain processing can be accomplished without requiring significant waiting time associated with processing from the perspective of the user.

Two important types of background processing that may be supported by the present invention are preprocessing and interim processing. Preprocessing refers to processing of an image that occurs prior to initial review of that image by a physician. As discussed below, such preprocessing may facilitate optimization of the displayed image or review workflow, i.e., the sequencing and timing of image display. Interim processing refers to background processing that occurs during a review session, e.g., in a lime period between initial review and a subsequent review of an image. Such preprocessing may be based on monitoring of the review process.

Thus, in accordance with another aspect of the present invention, digital mammographic images are automatically preprocessed prior to initial review by a physician. An associated process involves operating image acquisition equipment to acquire digital image information regarding a patient's breast and store the image information in an image repository, operating a processor to process the image information in background to provide processed image information, and making the processed image information available for subsequent initial review by a physician. The background processing of the image information involves executing at least one task for processing the image information free from any concurrent prompts from a user. A variety of different types of tasks may be performed in this regard including, for example, performing a diagnostic analysis of the image information, associating diagnostic information with the imaging information, optimizing certain display parameters of the imaging information and preparing images for display in accordance with a desired review workflow. In this manner, certain enhancement tasks can be performed prior to initial review by a physician for improved efficiency.

In accordance with a further aspect of the present invention, a mammographic image system is operated to prepare images for more rapid display during a review process. An associated method involves determining an anticipated sequence for an image review session by a physician; accessing an image repository to obtain image information corresponding to the anticipated sequence, and transferring the identified image information to a memory location for rapid display at a selected review station. The anticipated sequence may be determined based on an image review protocol for a particular physician, based on the type of medical process (e.g., mammographic screening or diagnosis), based on an initial analysis of the images to identify areas of possible interest to a physician, or based on other potentially predictive criteria. The logic for determining the sequence may be resident on an image review platform, a separate server or other location. The identified image information may be transferred to storage associated with the image review platform such as, for example, cache storage or may be retrieved from archive storage and stored in an active image repository. The images thus transferred are available for rapid display on the display terminal or terminals of the review equipment so as to reduce loading delay times otherwise associated with large image files.

According to another aspect of the present invention, mammographic image information is automatically preprocessed for optimized display. An associated process involves accessing image information from an image repository, identifying a display parameter relative to an image review process and optimizing the image information for display in connection with image review equipment based on the identified display parameter. Examples of optimization processes that may be performed in this regard include selecting and optimal monitor setting relative to a luminous range of a display device, optimally filling the viewing area of a display device, filling the available viewing area with a selected portion of the image and displaying the image in a known reference position or orientation to assist the physician in getting oriented to the image perspective. Such optimization logic may be executed by a processor resident at the image review site, at a central server, or at another location. Preprocessing of mammographic image information for optimal display increases the efficiency of the reviewing physician and reduces, eliminates or reverses a perceived disadvantage of digital imaging relative to film-based mammography.

In accordance with a still further aspect of the present invention, annotated instances of a digital mammographic image can be stored in an image repository. The associated mammographic image system includes an image repository; image review equipment for accessing images from the image repository; and logic for associating annotations with the image information to establish annotated image information and storing the annotated image information in the image repository. The annotations may be associated with the imaging information automatically or in response to user prompts. Thus, image information may be processed in background by a CAD utility to identify areas of interest and associate an annotation with those areas of interest. For example, the CAD system may perform a pixel-by-pixel or area-by-area analysis of an image to identify a potential microcalcification or other area of interest and superimpose a symbol on the image to identify the area of interest and the nature of the potential diagnosis. Alternatively, a physician may tag an image for later review. Thus, for example, a physician may perform an initial review of a large number of images corresponding to all of the patients who were screened on a given day. A subset of these images may be tagged by the physician (e.g., by selecting an appropriate icon or providing another input) for later review. These images can be readily recalled by the physician based on a search for tagged images. It will thus be appreciated that the annotation does not necessarily affect the visual display of the image. Additionally, images may be marked as reviewed, as may be desired.

BRIEF DESCRIPTION OF THE DRAWINGS

For a more complete understanding of the present invention, and further advantages thereof, reference is now made to the following Detailed Description, taken in conjunction with the drawings, in which.

DETAILED DESCRIPTION

In the following description, the invention is set forth in the context of a mammographic image system employing a distributed architecture based on a client server model. In particular, the invention is described below in connection with an implementation at a large medical facility that includes multiple mammographic image acquisition sites and multiple image review sites all associated with a central server and central image repository. While this implementation effectively illustrates the operation and advantages of the present invention, it will be appreciated that the invention is not limited to this implementation or similar contexts. For example, various aspects of the present invention are applicable to environments having a single image acquisition site and/or a single image review site. Additionally, it is not necessary that the acquisition equipment, review equipment and server be located at one site. In this regard, particular elements of the system or combinations of elements may be located at different sites that are interconnected by a wide area network or the like. Also, certain elements of the image processing discussed below may be conducted at an image acquisition site, an image review site, a server site or at another location or may be distributed across multiple platforms. Accordingly, the description that follows should be understood as exemplary and not as limiting the scope of the invention.

Figure 1:
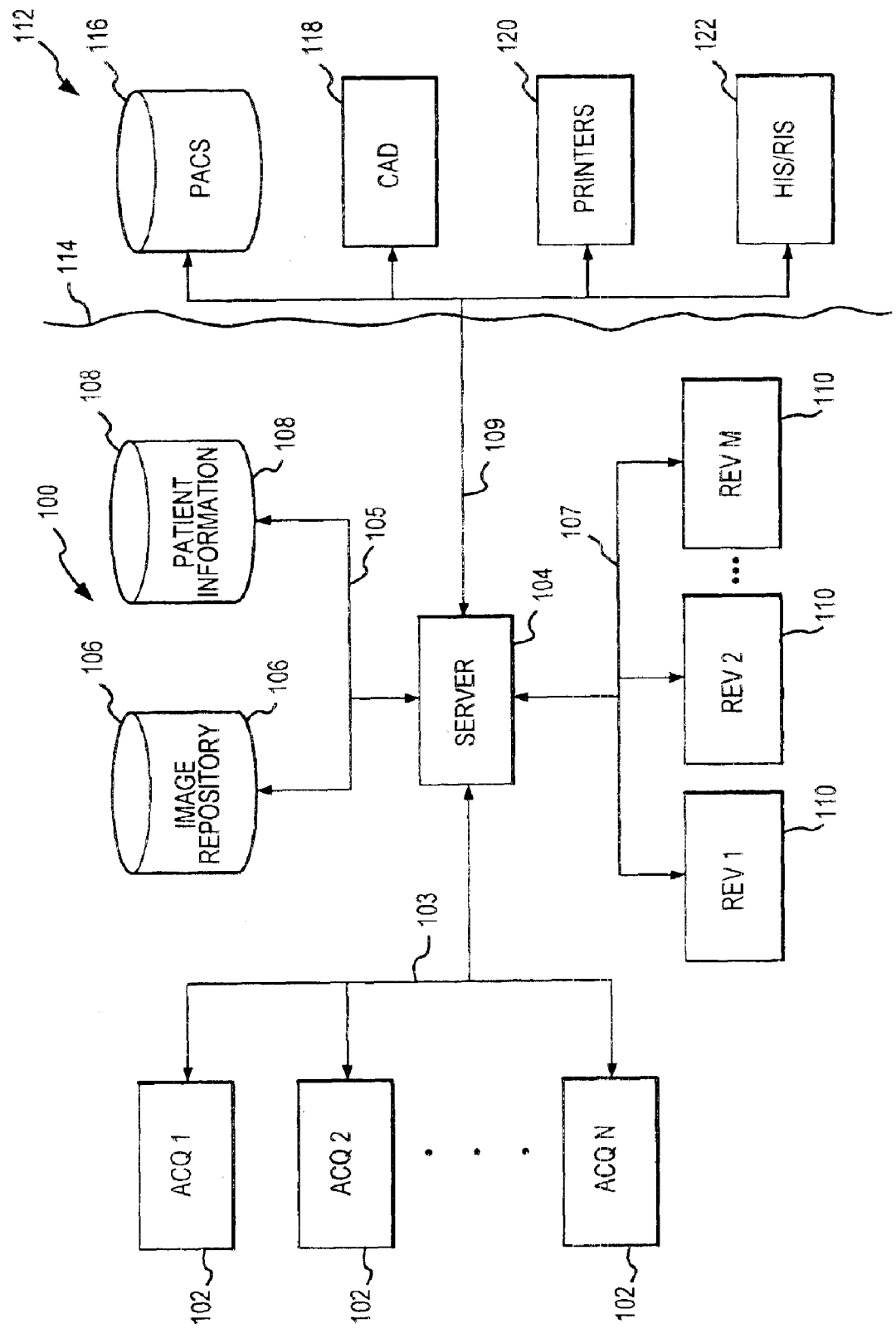
FIG. 1 is a schematic diagram of a mammographic image acquisition and review system in accordance with the present invention.

Referring first to FIG. 1, a mammographic image system 100 employing a distributed architecture is schematically illustrated. The system 100 generally includes a number (n) of image acquisition stations 102 and a number (m) of image review stations 110 all of which are associated with a central server 104. It will be appreciated that the number of image acquisition stations 102 and the number of image review stations 110 that may be supported within the mammographic image system 100 is substantially unlimited and the number of image acquisition stations 104 may not be equal to the number of image review stations 110. Indeed, it is anticipated that the numbers of these stations 102 and 110 often will not be equal but will be determined and occasionally changed based on work volume and other needs. Additionally, although a single central server 104 is illustrated, it will be appreciated that the server functionality discussed below may be distributed over multiple machines or platforms.

The image acquisition stations 102 are preferably interconnected to the server 104 by a wide bandwidth connection 103. This connection 103 may be provided as part of a Local Area Network or a Wide Area Network, e.g., a TCP/EP network. In addition, the image acquisition stations 110 are also preferably interconnected to the server 104 by a wide bandwidth connection 107. This connection 107 may also be provided as part of a Local Area Network or Wide Area Network. In the latter regard, the illustrated system architecture allows a physician to review images from a remote location, such as a reviewing station 110 at a physician's office separate from the medical facility that includes the acquisition stations 102, or to review images from multiple acquisition stations 102 located at different medical facilities from one another.

The illustrated server 104 is operative to access an image repository 106 and patient information database 108, as will be discussed in more detail below. It is also operative to access a number of DICOM tools 112 via a standard DICOM interface 109. These tools 112 are schematically illustrated as residing behind a DICOM boundary 114 associated with the interface 109, but may physically reside at a local or remote location. A variety of such DICOM tools are available. The illustrated tools 112 include a picture archiving and communication system (PACS) database 116, a computer aided design (CAD) diagnostic tool 118, printers 120 and a hospital information system (HIS)/radiology information system (RIS) 122.

The stations 102 and 110 will be described in more detail below. The image repository 106 stores image information from the image acquisition stations 102 and the patient information database 108 stores associated patient information. The illustrated repository 106 and database 108, though schematically illustrated as separate components, are configured to form a composite searchable database structure such as a relational database system and may physically be embodied in any of various high-capacity data storage systems, such as a RAID system. That is, the images of the repository 106 are indexed to the patient information of database 108 and the patient information is organized in tables of cross-indexed data fields. Such fields may include information identifying the patient, the available images, the dates of images (study), the facility where the images were acquired, the technicians involved in the image acquisition, whether the images have been reviewed, any annotations or annotated image versions, the reviewing physician, and any other information that may be of interest.

This database structure may be searched by field(s) using a database management tool associated with server 104. Such tools are well known. For instance, by using such a tool a reviewer at an image review station 110 can query the database structure to obtain all images for a given patient or all such images acquired within a given date range. Alternatively, a physician may obtain all images acquired on a given date, all images for all patients acquired on a given date and associated with a particular acquisition station or stations 102, or all images for all patients acquired on a given date and associated with an identified physician. Moreover, the search tool can be used to improve diagnosis or prognosis. In this regard, the database may be searched based on image features such as microcalcifications, mass, mass location etc. such a search may be conducted based on physician annotations, CAD annotations or other indications of the feature of interest. In this manner, similar images or image portions, or files that re otherwise of interest may be readily accessed by using the search tool.

The database structure may be used for purposes other than patient analysis. For example, the database structure may be queried by technician or acquisition site to obtain information regarding work performance or efficiency or to correct any recurring image acquisition or processing errors. The illustrated connection 105 between the server 104 and the repository 106 and database 108 may be, for example, an internal server connection (e.g., a data bus), a LAN connection or a WAN connection.

The illustrated DICOM tools 112 include a picture archiving and communication system (PACS) database 116. This database 116 is used to archive images that do not need to be kept in the repository for immediate access, but which may be desired for review. For example, a physician reviewing images for a patient may wish to review current images together with old images from a prior screening or screenings to identify any changes or signs of advancement of a condition. Such older images may be recalled from the PACS database 116 via the DICOM interface 109. Alternatively, such images may be stored, for example, on a storage device accessible at a review station 110 such as a magneto-optical (MO) drive. In either case, such archiving frees repository resources while providing flexibility for physicians to construct desired review workflows as discussed below. Moreover, the physician workflow protocols and other predictive logic of the system 100 allow the server 104 to predictively retrieve images from the repository 106 and database 116 as a background task for prompt display during a review session.

CAD tool 118 may be any of various commercially available, computer-based medical image analysis and diagnostic tools. These tools typically analyze a single image or multiple images, such as on a pixel-by-pixel basis to identify any features that may have diagnostic significance and apply diagnostic algorithms or heuristic engines to determine a possible diagnosis. In the context of mammography, such tools may identify a suspicious mass, e.g., based on a locally reduced detected signal intensity, and may further identify the possible nature of the mass (e.g., microcalcifications) based on features of the mass. Corresponding information may be annotated on the image. For example, a graphic such as a particular geometric shape (e.g., a cone or triangle) may indicate a particular potential condition and the location of the graphic on the image may indicate the location of the condition. A physician may use the graphic to zoom in on or otherwise further review the area of interest. Such an enlarged image may be automatically retrieved or otherwise prepared for display at station 110, e.g., stored in cache at the station 110. Thus, when the physician selects the associated graphic (which may comprise a graphical user interface element superimposed on the image), an associated image may appear instantaneously. This image may be optimized based on the nature of the associated condition of interest, e.g., enlarged, contrast/brightness enhanced, edge detection enhanced, etc.

In accordance with the present invention, the CAD tool 118 can be used for preprocessing images or otherwise automatically processing images, e.g. in the background during a review session. In this regard, the server 104 may be programmed to automatically, upon receiving an acquired image from any of the acquisition stations 102, store one instance of the image (e.g., the raw image information) in the image repository and forward another instance or copy of the image to the CAD tool 118. This latter instance of the image may be formatted in accordance with standards of the DICOM interface 109. The image is then processed by the CAD tool 118 as discussed above and the processed image, including CAD annotations, is stored by the server 104 in the image repository 106 and indexed to the original image and corresponding patient information.

All of the noted CAD processing can occur automatically prior to the initiation of a review session by a physician. Accordingly, if desired, when the physician enters a query to gather images for a review session, the CAD-processed images may be provided from the image repository. The physician may alternatively or additionally access the raw (unpreprocessed) image, e.g., for comparison/confirmation purposes.

Similar CAD processing may occur during or after a review session. For example, upon an initial screening of an image, a physician may note a suspicious mass in the patient's breast. The physician may then tag the image or a location on the image for CAD processing so as to obtain the benefit of the CAD diagnostic tool. The user interface of the review station 110 may have defined keystrokes or graphical interface elements to facilitate such tagging. In response to these inputs, the processor of the review station 110 transmits the image or image portion to the server 104 which reformats the image information as necessary and forwards the information to the CAD tool 118 for analysis.

The server 104 or a processor of the review stations 110 may execute predictive algorithms, in connection with the noted CAD processing or otherwise, to anticipate the needs of the reviewing physician and improve workflow. In connection with CAD processing, the server 104 may monitor CAD processed images to anticipate such needs and automatically, as a background task, prepare enhanced images for display. For example, where a CAD annotation is included in the processed image indicating and characterizing a potential condition of interest, an enlarged view of the relevant image section with display parameters (e.g., contrast, brighteners, and enhanced edge definition) appropriate for the characterized condition may be prepared for automatic display on a monitor of the station 110 or may be stored for display upon receiving a prompt from the user. As discussed below, images may be prepared for display in a similar fashion based on protocols defined for a user, user type, review type or the like. Such protocols may also be developed or supplemental for a particular physician or on a user independent basis, using logic to monitor acquisition and review processes to empirically or heuristically learn patterns that may be used to predict physician needs.

The DICOM tools 112 also include printers 120 in the illustrated embodiment. These printers 120 receive image information via the DICOM interface 109 and provide hard copies of the images, e.g., on paper or transparencies for review on a light box or the like. This allows physicians the option of reviewing hard copy images and facilitates patient discussions in an office environment.

The HIS/RIS tool 122 provides access to HIS/RIS systems. The HIS/RIS systems include databases of patient information such as appointment dates and times and other information that may be imported into the patient information database 108 and used for populating fields of the image acquisition and image review protocols as discussed below, as well as in fashioning queries for image information. This information is readily handled by the processor 104 based on the DICOM standard. As will be appreciated by those skilled in the art, DICOM (Digital Imaging and Communications in Medicine) provides an industry standard for the exchange of digital imaging related information.

The server 104 or processors of the image review stations 110 may also execute logic for image display optimization. Such optimization may relate to optimally using the available display area for displaying the selected images (e.g. selecting a landscape, portrait, or other orientation, sizing the images, selecting zoom settings and image portions, and establishing a reference position or orientation for images to assist the physician), optimally setting display parameters (brightness, contrast, edge enhancement, etc.) or optimizing any other display-related characteristics. Such functionality may be executed based on defined workflow protocols, CAD, or other annotations or other information available to the relevant processor(s). In this regard, optimization of a luminescence setting may be performed relative to a specific image or image portion. This may depend on a number of factors. For example, a human's ability to distinguish shades is dependent on the location of such shades within a gray scale range. That is, the ability to discern shades is not a linear function with respect to gray scale such that a given shade increment may be more readily distinguished by a viewer at a given point on the gray scale than the same increment at a different point on the gray scale. Presenting the image at an optimized luminescence may therefore enhance the viewer's ability to distinguish features of interest. So, the luminescence setting may be selected based on CAD or physician annotations indicating a condition of interest and may also take into account tissue density, source settings, exposure and other factors affecting optimal display parameters. Such display optimization may also take into consideration the size and resolution of the display as well as the display's aspect ratio including, in the case of rotatable displays as discussed below, whether the display is currently in a landscape or portrait orientation.

Additionally, special filtering may be used to optimize display parameters relative to specific areas of an image. For example, specific zoom or enlarged views of particular image areas may be provided, for example, based on a CAD annotation indicating a condition of potential interest. Moreover, the image resolution may be varied based on a feature of interest associated with a specific image area. Thus, a 25 mm resolution (as is available in the noted SenoScan system of Fischer Imaging) may be provided for an image area where microcalcifications re indicated and a lesser resolution may be provided for areas where a mass is indicated or where no annotation is indicated. This allows for reducing the size of the image file to be loaded so as to improve processing speed while providing high resolution where it may be desired. Relatedly, a high resolution mode or lower resolution mode may be determined by the processing logic for an overall image, or may be selected by a user as part of a protocol definition.

As noted above, the server 104 may store multiple instances of an image in the repository 106. Such instances may include CAD-processed images and user annotated instances. The user may annotate an image to mark the image as reviewed, identify areas of interest on the image, or include other information. Additionally, a user may utilize the server 104 to store a user-processed image or image portion that is enlarged, edge-enhanced, or otherwise modified based on user inputs. Alternatively, image modification information may be stored and indexed to an image so that modified images can be constructed as needed. Relatedly, high resolution and lower resolution versions of an image may be used for different purposes. For example, a high resolution version may be provided to a CAD system for enhanced analysis and a lower resolution version may be provided to a review station for display so as to reduce the file size and loading times.

The server 104 may also make a single image or copies of the same image available to multiple review stations 110. This may be desired for concurrent independent work or collaborative work. In the latter regard, the server 104 may include conventional collaboration logic for allowing multiple users to work on a common document and see changes entered by the other collaborator(s). Such collaboration may improve diagnosis.

Figure 2:
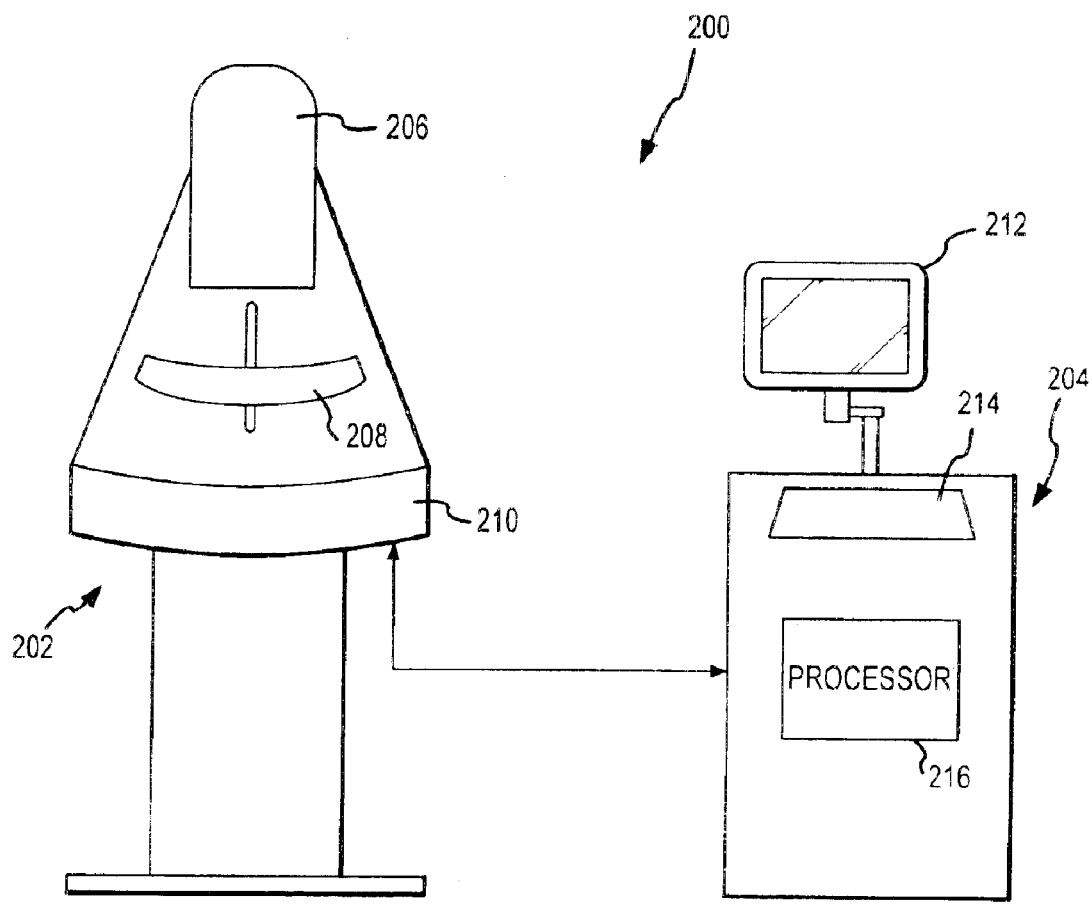
FIG. 2 is an image acquisition station of the system of FIG. 1.

An example of an acquisition station 200 is illustrated in FIG. 2. The station 200 generally includes an imaging device 202 and a control module 204. The illustrated imaging device 202 is an x-ray-based mammography system such as the SenoScan system marketed by Fischer Imaging Corp. of Thornton, Colo. Such imaging systems generally include an imaging source 206 such as an x-ray tube, an imaging detector 210 such as a direct x-ray detector or a phosphorescent element associated with a light detector. The illustrated device 202 further includes a compression paddle 208 that is vertically movable to immobilize and flatten, to an extent, the patient's breast for improved imaging. The paddle 208 is preferably substantially transparent to the imaging signal. In the case of the noted SenoScan system, the source 206 can be rotated to scan a fan beam of x-rays across the patient's breast. The detected x-rays are then electronically combined to form a substantially full field composite image of the patient's breast. The illustrated processing module 204 includes a user interface 214 such as a keyboard and mouse for receiving user inputs, a local monitor 212 for displaying near real-time images acquired by the device 202 and a processor 216.

During a screening procedure, a physician or clinician may direct the process via inputs using the user interface 214. The inputs may identify the patient, the image projection view, the examination date, certain imaging parameters and any other information of interest. The interface 214 can also be used to initiate exposures and otherwise manage the image acquisition workflow. These inputs are received by the processor 216 which operates the imaging device 202, directly or in response to inputs from a server. The processor 216 also receives digital image information from the detector 210 and executes logic for forming a composite image for display on the monitor 212 and transmits the image information together with associated patient data and any other desired information to the server 104 (FIG. 1).

Figure 3:
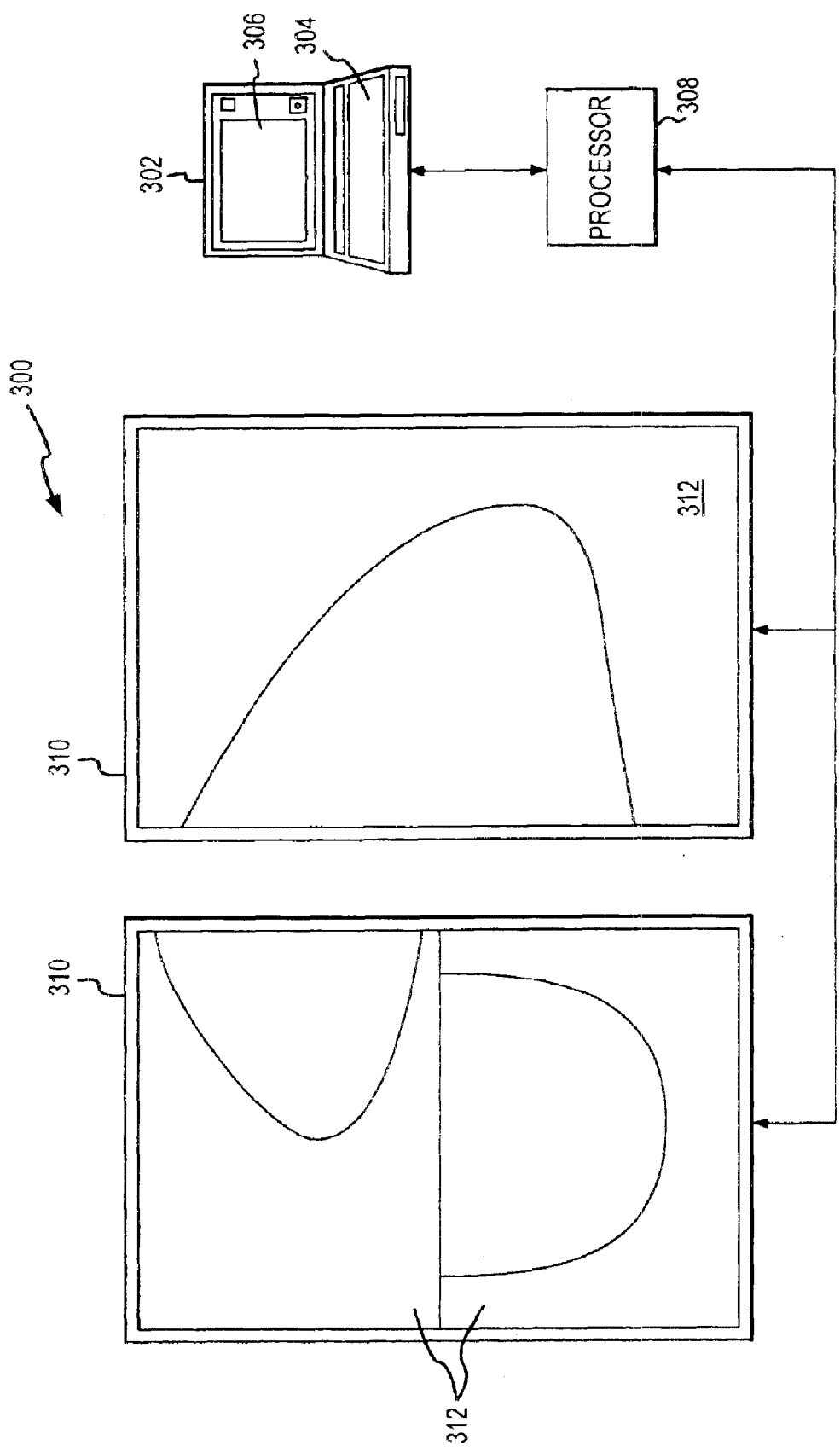
FIG. 3 is an image review station of the system of FIG. 1.

FIG. 3 schematically illustrates an image review station 300. The illustrated image review station 300 includes a workstation 302, a processor 308 and display monitors 310. More specifically, the workstation 302 includes a user interface 304 such as a keyboard and mouse for allowing a user to manage workflow during an image review session. The workstation 302 also includes a display 306 for displaying certain information and managing review session workflow as will be discussed in more detail below. Based on input from the workstation 302 the processor 308 causes images 312 to be displayed in the display area of the monitors 310. The illustrated monitors are high-resolution large format monitors. The monitor display area may be divided into multiple regions for displaying multiple images as may be desired by a physician.

Figure 4:
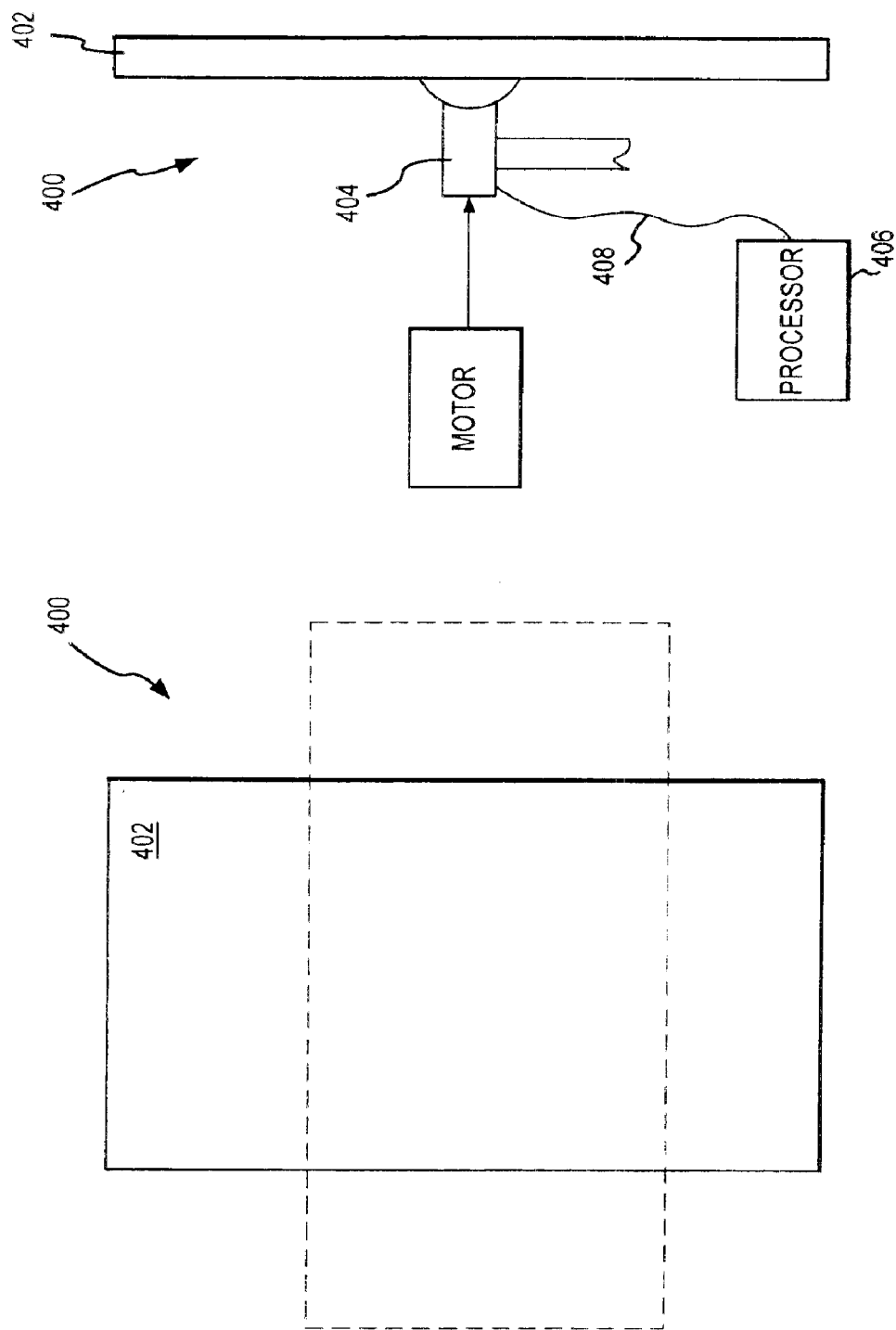
FIGS. 4A–4B are front and side views respectively of a monitor of the review station of FIG. 2.

As noted above, the mammographic image system may include at least one monitor, e.g., at an acquisition station or review station, that is rotatable. A physician may desire to rotate a monitor so as to obtain a different viewing area aspect ratio for viewing images arranged in a particular pattern or format. Such a rotatable monitor 400 is generally illustrated in FIGS. 4A and 4B, the illustrated monitor 400 includes a flat panel display 402 mounted on a rotatable mount 404 that communicates with a processor 406 of a review station via a communications link 408. The mount 404 allows the display 402 to rotate between at least landscape (shown in phantom in FIG. 4A) and portrait orientations. In this regard, the mount 404 preferably includes recesses, detents or the like for registering and locking into each of the orientations in lazy-Susan fashion.

The orientation of the illustrated display 402 is reported to the processor 406 via link 408. For example, where the mount 404 includes a detent associated with each of the orientations, the orientation of the screen may be detected based on deployment of the detent associated with position registration (which may be converted to an electric signal via a contact switch). More sophisticated feedback mechanisms such as involving encoders may be employed to provide detection of a range of orientations. In any event, this orientation information can be used by the processor 406 or the server to appropriately orient displayed images, e.g., to orient images so that annotations or markings are right-side-up or to otherwise provide the desired image orientation with due regard for the current display orientation. Moreover, the display orientation may be automatically taken into consideration in sizing or orienting images so as to optimally utilize the display area. The display orientation may also be defined by a physician as part of an image review protocol. A motor 410 may be provided to automatically rotate the monitor 402 to the desired orientation. Moreover, the orientation of the monitor may be selected by the user as part of a protocol definition or selected by processing logic, e.g., to optimize monitor space utilization for a given layout of multiple images.

Figure 5:
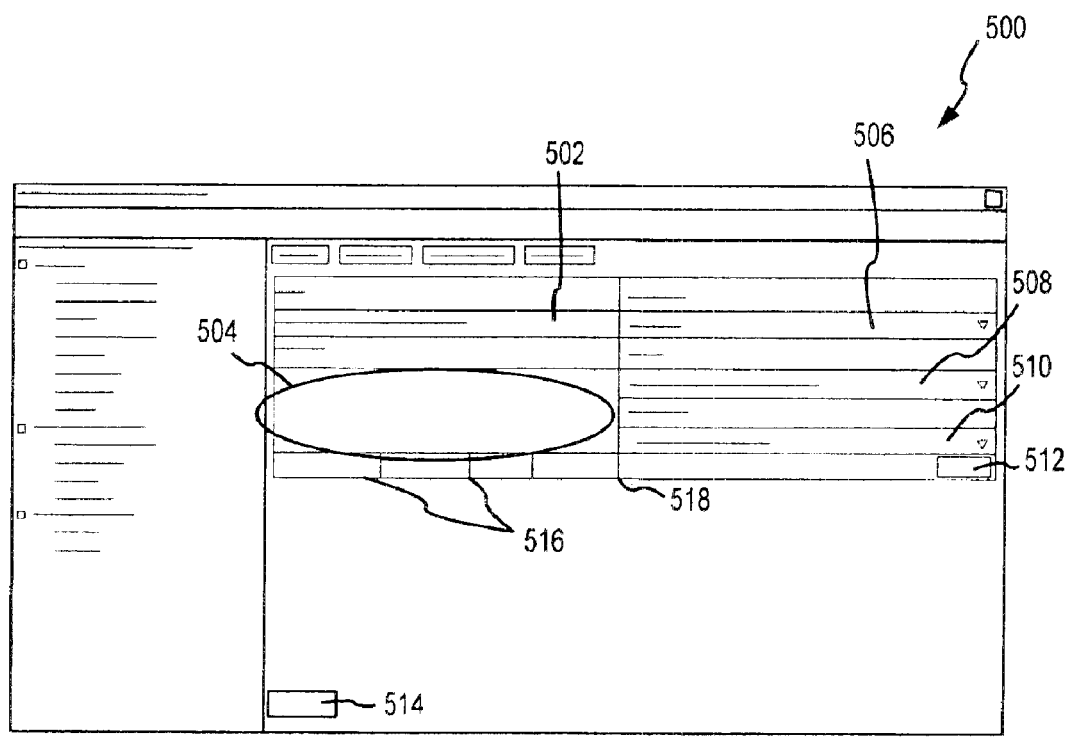
FIGS. 5–7 are user interface screens used in the system of FIG. 1.
Figure 6:
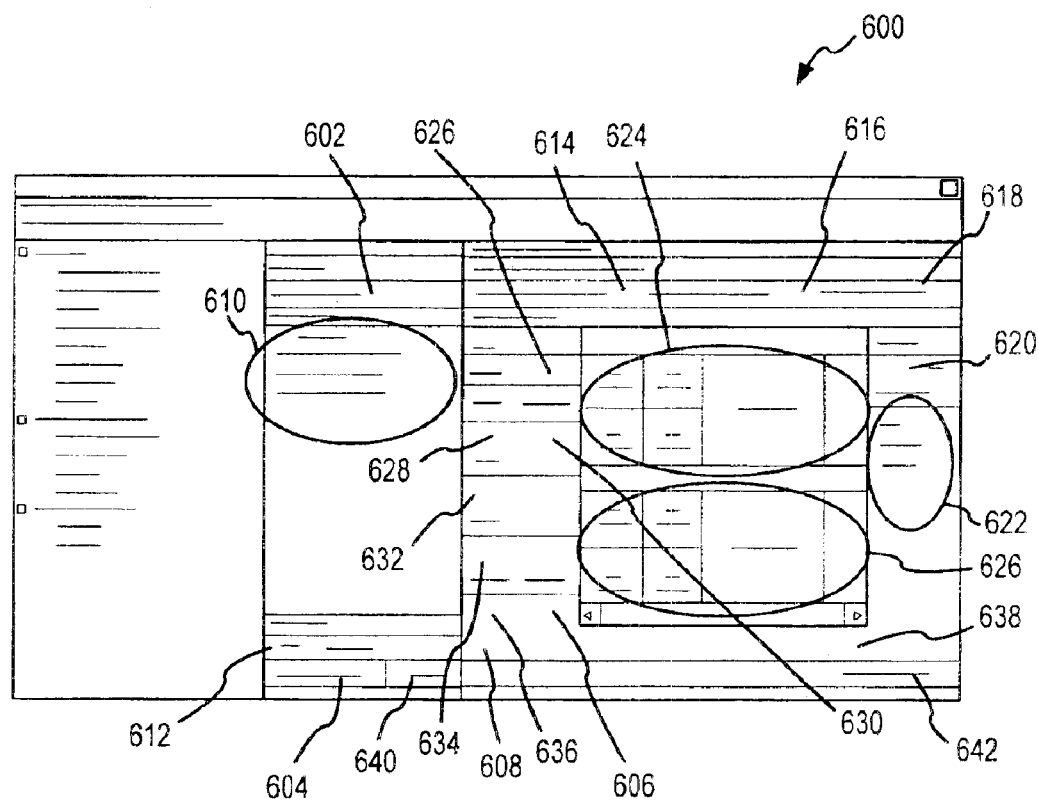
Figure 7:
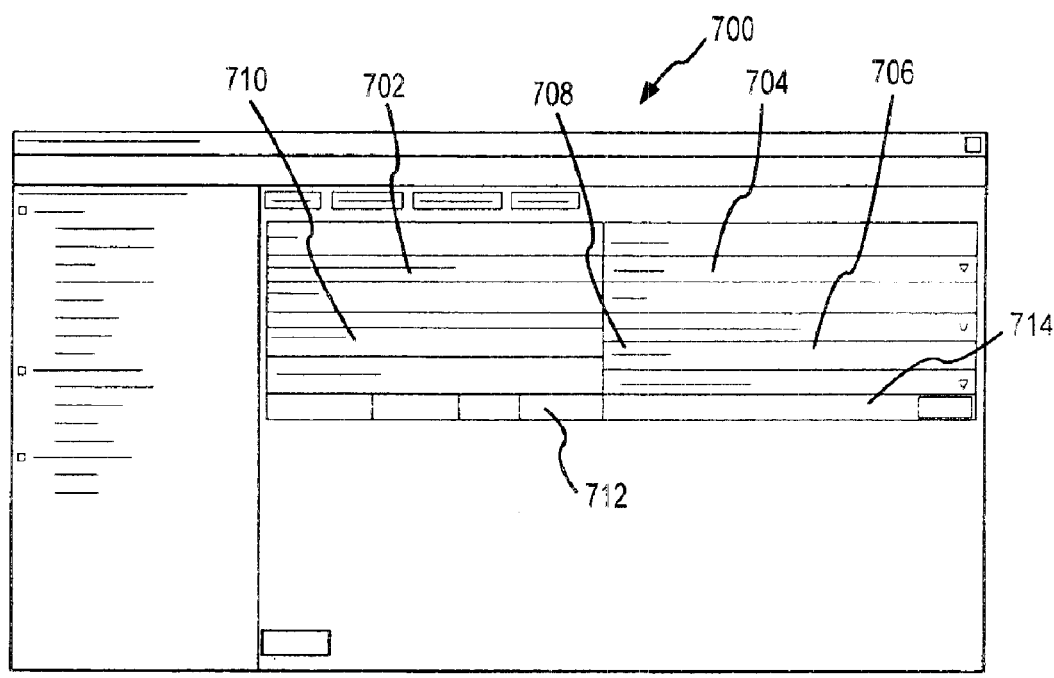

In connection with the monitors of the image acquisition stations and the image review stations, a number of screens may be provided to enable the user to define patient studies, and define workflows. FIGS. 5–7 illustrate exemplary user interface screens in this regard. It will be appreciated that alternate user interface implementation may be used to provide corresponding functionality. The logic for defining the screens, receiving and processing inputs from the screens and implementing associated functionality may be performed at an image acquisition/review station or at a server(s) or may be distributed as between the station and server(s).

Referring to FIG. 5, a projection screen 500 is illustrated. This screen is used to set the image projection preferences by type and sequence, for example, for each individual user, station, or type of user or procedure. In the case of user-specific protocols, the preferences set on this screen are automatically associated with the specific user when that particular user accesses the acquisition screen. This causes the exam to automatically increment to the next projection in sequence as each projection is acquired.

The users drop down menu 502 shows the users and types of users that have been authorized to operate the image acquisition equipment. Users listed in this menu have been previously stored in the database.

To establish a projection listing for a particular user, the name of the user can be selected from the drop down menu to cause the selected name to appear in the header field at the top of the menu. The user may then construct the sequence listing for the selected user by using several of the illustrated screen features.

The user's sequence listing 504 shows the types of projections selected for association with the indicated user. The selections are added to the user sequence listing by selecting the projection attributes from the laterality 506, view 508, and modifier's 510 drop down menus and then clicking on the add button 512. Projections can be revised, added, removed, or reordered in this listing until the screen entries are saved into the system database by means of the save button 514. As the listing is being added to, the order in which a particular projection appears in the sequence can be changed by first selecting the projection in the listing, then clicking on the move up or move down button 516 as required.

The laterality drop down menu 506 allows the user to select the laterality of the projection. Selections include left, right, and both.

The view drop down menu 508 allows the user to select the view that is to be combined with the laterality as selected from the laterality drop down menu 506. The views that may be selected include medio-lateral, medio-lateral oblique, latero-medial, latero-medial oblique, cranial-caudal, cranial-caudal from below, superolateral to inferomedial oblique, CC exaggerated, CC exaggerated laterally, and CC exaggerated medially.

The modifiers drop down menu 510 allows the user to further modify the laterality and view selected. The modifiers that may be selected include magnification, clevage, axillary tail, rolled lateral, rolled medial, rolled superior, rolled inferior, implant displaced, spot compression, and tangential.

The add button 512 allows the user to add the projection, as thus defined, to the user's sequence listing.

The move up and move down buttons 516 allow the user to change the order in which the selected projections appear in the user's sequence listing 504. The remove button 518 allows the user to remove a projection from the user's sequence listing 504. Finally, the save button 514 saves the projection list for the indicated user to the system database.

FIG. 6 illustrates a screen 600 that can be used to program one or more preferred workflow sequences into the system for each user, type of user, or type of examination/study. These sequences can be used during image acquisition to automatically select the patient lists and ordering of patients at the appropriate acquisition workstation for each exam. During exam review, the workflow sequence automates the display of selected exam images on the review station monitors. It will be appreciated that these workflows may be used by the server to retrieve images from the image repository and download the appropriate images to the review workstation. The review workstation processor may load these images in sequence in cache so that the images can be quickly displayed, thereby reducing review timeframes. Workflows may also be constructed during image acquisition or image review by a user while in the patient information screen at either the acquisition or the review workstation.

The process for defining workflows may be understood by reference to the workflows screen 600 as shown in FIG. 6. Generally a workflow includes a filter of patients (e.g., all patients who had exams on a given day), a filter of the studies for a particular patient (e.g., the current study plus the study from the previous year), and a sequence of display protocol. Construction of a new workflow begins with the selection of the user associated with the workflow. This selection is made from the users select menu 602. The selected user may be an individual registered to use the system, or a type of user, such as administrator, technologist, or physician.

The new workflow button 604 is used to enter a descriptive name for the new workflow configuration. From the patient progression area of the screen, the patients, studies, and viewed criteria that is to be used to select images for the new workflow can be selected. These selections determine the category of patients, the number of studies per patient, and which of the previous studies are to be selected.

The user may then define the protocol that is to be used for the first image projection and the new workflow. This protocol defines the overall configuration and progression of image formats that will be automatically displayed in sequence as the user increments through the review session. To define this protocol, the user selects the type for the first image display. The types that may be selected include blank, selected, or custom. If the user selects custom, the user may then specify the number of images that are to be displayed on the screen, by the number of rows and columns in which the exam images will be displayed. For example, the user can specify a screen display that can accommodate any desired format including ranges from, for example, one row by one column for a total of one image, up to three rows by three columns for a total of nine images in one implementation. The user may also select other image modifications that impact the workflow display format, such as view, tools, and zoom.

The user may then select the study number from which the images are to be selected for inclusion in the workflow. The display select menu 606 can then be used to select the display on which this image and the workflow is to be displayed. Once all the selections and image modifications have been made, the add button 608 can be used to add the current image configuration to the workflow. A box will appear in the display field selected from the display select menu 606. Each time the above process is repeated a new box will be displayed in the selected display field. If a specific projection is to be displayed at a particular step in the workflow sequence and on a particular display, it may be selected from the projection field and dragged to the desired location.

The screen illustrated in FIG. 6 includes a number of features for assisting in the workflow definition. The users select menu 602 shows the users and types of users that have been authorized to operate the system. These are the same users that have been stored in the system database as discussed above. The workflow listing 610 displays the default screening and diagnostic workflows and any custom workflows that have been created for specific users or types of users. The new workflow button 604 is used to initiate the construction of a new workflow. The description field 612 allows the user to enter a name for the new workflow that is being created.

The patients select menu 614 allows the user to select a category of patients to be filtered by the workflow algorithm. Available selections include all today's work, all pending work, all today's unread, all pending unread, user's today's work, and user's pending work. The studies select menu 616 provides a listing of studies from which images may be selected. The viewed select menu 618 allows the user to select images from specific exam histories that are to be included in the workflow. In this regard, it will be appreciated that particular users may wish to review current images against images from prior exams. The study number menu 620 allows the user to specify the exam study histories from which the images are to be obtained. These selections correspond to the number of exams for which images are available. The projection field 622 displays the projections that exist for each patient exam included in the studies selected for inclusion in the workflow.

The protocol may be defined in relation to any number of monitors that may be provided at an image review station. In this regard, the illustrated display 1 and display 2 fields 624 and 626 display the constructive workflow for a two monitor station. The workflow is presented as a series of blocks, each block representing a single screen display. The actual format or configuration of each block in the workflow is determined by the type, view, tools, zoom, and display selections selected by the user prior to adding the block to the workflow.

The display select menu 606 allows the user to select the display field into which the next workflow element will be added. This determines which monitor will display the image currently being added to the workflow sequence.

The type select menu 626 allows the user to specify the type of display to be added to the workflow sequence. Selections include blank, selected, and custom. If blank is selected, the specified monitor will display a blank screen for this step in the workflow. If selected is chosen, the specified monitor displays the image format that is the next image in the selected study for this step in the workflow or the image selected by the current button press to provide the desired enhancement, e.g., full resolution display. If custom is chosen, the specified monitor will display the image display format that meets the criteria established by this workflow. When custom is selected, the rows 628 and columns 630 buttons are active. The rows button 628 determines the number of rows of images that will be displayed on the monitor and the column button 630 determines the number of columns.

The view select menu 632 allows the user to specify how the image is fitted to the display. Selections include full resolution, fit width, fit height, fit window ("auto size"). In this manner, the available monitor space can be effectively utilized, with due regard for monitor orientation in the case of rotatable monitors.

The tools select menu 636 allows the user to select tool features that are to be applied to the image when it is displayed. The tools that may be selected include zoom, processed, annotation, CAD, patient information, invert, flip horizontal, flip vertical.

The zoom select menu 636 is used when the zoom tool is active to select a zoom multiplier. For example, zooms of 2× thru 6× may be selected.

When a user has made all the desired selections and modifications for the next element to be added to the workflow, the add button 608 may be used to save the element definition. The remove button 638 may be used to delete an element from the workflow. Finally, once the user is satisfied with the formatting and sequencing of the workflow, the save workflow button 640 can be used to save the workflow into the system database. It will be appreciated that this workflow information may be used for retrieving and caching images for improved image review efficiency. The remove workflow button 642 is used to remove and entire workflow from the system database. A start button (not shown) can be used to start a newly selected workflow sequence.

FIG. 7 illustrates a user interface screen 700 that allows the user to define the search criteria used to create the work list of patient examinations from appointment information that has been entered into the facility's HIS/RIS system. To create a work list, the user enters the date and time of the first and last scheduled appointments to appear on the work list and selects import. All scheduled appointments that fall within the date/times entered into the start date and end date fields will be imported into the system database from the HIS/RIS system. This screen 700 can be used to set work list criteria for acquisition station and review station operations. In this regard, the server may be utilized to access the HIS/RIS system and thereby define such operations.

FIG. 7 illustrates a number of screen features for the work list screen. The start date field 702 is used to enter the date and time for the first scheduled patient exam to appear on the work list. The end date field 704 is used to enter the last scheduled exam that is to appear on the work list. The patient reference number field 706 allows for searching the HIS/RS database for the patient exam identified by the reference number entered into the field. This allows a user to access a specific patient record. The patient reference number check box 708 is used to enable a search for the patient record associated with the reference number entered in the patient reference number field. The station HIS/RIS identification name drop down menu 710 allows the user to select the workstation where the extracted work list will be used. The HIS/RIS provider drop down menu 712 allows the user to select the HIS/RIS database from which the patient appointment work list will be extracted. The user to assign selected work items pop up menu 714 allows the user to select the user to which the work list is assigned. All users authorized to use the system are included in the pop up menu selections. Finally, after all field entries have been made, an import button (not shown) is used to import the results of the work list search into the system database.

Those skilled in the art will now see that certain modifications can be made to the apparatus and methods herein disclosed with respect to the illustrated embodiments, without departing from the spirit of the instant invention. While the invention has been described above with respect to the preferred embodiments, it will be understood that the invention is adapted to numerous rearrangements, modifications, and alterations, and all such arrangements, modifications, and alterations are intended to be within the scope of the appended claims.

What is claimed:

1. A mammographic imaging system, comprising:

mammographic image acquisition equipment, including an imaging source for transmitting an imaging signal to a patient's breast, a detector for receiving said transmitted signal from the patient's breast and providing a digital signal based thereon, said digital signal defining a first digital image of at least a portion of said patient's breast;

at least one processor for obtaining first image information including information corresponding to said first digital image, automatically processing said first image information to provide first processed image information different from said first image information and making said first processed information available for review by a user;

said at least one processor running logic, in connection with said automatic processing, for identifying at least one task to be executed in connection with said first image information for controlling a display of said first image information, and executing said task to provide said first processed information, said task being automatically identified and executed by said at least one processor free from any concurrent user prompts related to said task; and mammographic image review equipment including at least one monitor for displaying a mammographic image based on said first processed image information.

2. A mammographic imaging system as set forth in claim 1, wherein said at least one processor is operative for performing said automatic processing prior to initiation of an image review session by a user.

3. A mammographic imaging system as set forth in claim 2, wherein said at least one processor is operative for performing said automatic processing during an image review session by a user.

4. A mammographic imaging system as set forth in claim 1, wherein said at least one processor is operative for performing said automatic processing by employing a diagnostic tool for processing said first digital image for diagnostic purposes.

5. A mammographic imaging system as set forth in claim 1, wherein said at least one processor is operative for performing said automatic processing by associating diagnostic information with said first image information to provide said first processed image information.

6. A mammographic imaging system as set forth in claim 1, wherein said first image information includes information corresponding to multiple digital images and said at least one processor is operative for performing said automatic processing by preparing information corresponding to said multiple images for display in accordance with a desired workflow.

7. A mammographic imaging system as set forth in claim 6, wherein said preparing involves determining a sequence for displaying said images.

8. A mammographic imaging system as set forth in claim 7, wherein said workflow is based on a user definition and said sequence is determined by reference to said user definition.

9. A mammographic imaging system as set forth in claim 7, wherein said sequence is determined by monitoring an image review session.

10. A mammographic imaging system as set forth in claim 1, wherein said at least one processor is operative for performing said automatic processing by moving said imaging information from a first storage location to a second storage location.

11. A mammographic imaging system as set forth in claim 1, wherein said at least one processor is operative for performing said automatic processing so as to achieve optimization of a display of said first image information by said mammographic image review equipment.

12. A mammographic imaging system as set forth in claim 11, wherein said optimization involves selecting a display orientation for orienting an image on said monitor.

13. A mammographic imaging system as set forth in claim 12, wherein said display orientation is selected based on an input regarding an orientation of said monitor.

14. A mammographic imaging system as set forth in claim 1, wherein said optimization involves selecting a value of a display parameter for said monitor.

15. A mammographic imaging system as set forth in claim 14, wherein said display parameter comprises one of a luminous range of said monitor and a contrast of said monitor.

16. A mammographic imaging system as set forth in claim 11, wherein said optimization involves maximizing use of an available monitor area for displaying said mammographic image.

17. A mammographic imaging system, comprising:

mammographic image acquisition equipment, including an imaging source for transmitting an imaging signal to a patient's breast, a detector for receiving said transmitted signal from the patient's breast and providing a digital signal based thereon, said digital signal defining a first digital image of at least a portion of said patient's breast;

at least one processor for obtaining first image information including information corresponding to said first digital image, automatically preprocessing said first image information to provide first preprocessed image information different than said first image information, and making said first preprocessed information available for review by a user;

said mammographic image review equipment being operative by a user for supporting a review session by the user involving the review of one or more images, said review sessions being initiated by said user by entering, a command to access said system and being terminated by said user by entering a command to exit said system, and said processor is operative for performing said automatic preprocessing prior to initiation of said image review session by said user;

said at least one processor running logic, in connection with the automatic preprocessing, for identifying at least one task to be executed in connection with said first image information for controlling a display of said first image information and executing said task to provide said first preprocessed information, said task being automatically identified and executed by said at least one processor free from any concurrent user prompts related to such task; and mammographic image review equipment including at least one monitor for displaying a mammographic image based on said first processed image information.

18. A mammographic imaging system as set forth in claim 17, wherein said at least one processor is operative for performing said automatic preprocessing by employing a diagnostic tool for processing said first digital image for diagnostic purposes.

19. A mammographic imaging system as set forth in claim 17, wherein said at least one processor is operative for performing said automatic preprocessing by associating diagnostic information with said first image information to provide said first processed image information.

20. A mammographic imaging system as set forth in claim 17, wherein said first image information includes information corresponding to multiple digital images and said at least one processor is operative for performing said automatic preprocessing by preparing information corresponding to said multiple images for display in accordance with a desired workflow.

21. A mammographic imaging system as set forth in claim 20, wherein said preparing involves determining a sequence for displaying said images.

22. A mammographic imaging system as set forth in claim 21, wherein said workflow is based on a user definition and said sequence is determined by reference to said user definition.

23. A mammographic imaging system as set forth in claim 21, wherein said sequence is determined by monitoring an image review session.

24. A mammographic imaging system as set forth in claim 17, wherein said at least one processor is operative for performing said automatic preprocessing by moving said imagine information from a first storage location to a second storage location.

25. A mammographic imagine system as set forth in claim 17, wherein said at least one processor is operative for performing said automatic preprocessing so as to achieve optimization of a display of said first image information by said mammographic image review equipment.

26. A mammographic imaging system as set forth in claim 25, wherein said optimization involves selecting a display orientation for orienting an image on said monitor.

27. A mammographic imaging system as set forth in claim 26, wherein said display orientation is selected based on an input retarding an orientation of said monitor.

28. A mammographic imaging system as set forth in claim 25, wherein said optimization involves selecting a value of a display parameter for said monitor.

29. A mammographic imaging system as set forth in claim 28, wherein said display parameter comprises one of a luminous range of said monitor and a contrast of said monitor.

30. A mammographic imaging system as set forth in claim 25, wherein said optimization involves maximizing use of an available monitor area for displaying said mammographic image.

* * * * *